United States Patent
Meister et al.

(10) Patent No.: US 10,493,273 B2
(45) Date of Patent: Dec. 3, 2019

(54) BILATERAL MATCHING OF FREQUENCIES AND DELAYS FOR HEARING IMPLANT STIMULATION

(71) Applicant: MED-EL Elektromedizinische Geraete GmbH, Innsbruck (AT)

(72) Inventors: Dirk Meister, Innsbruck (AT); Peter Schleich, Telfs (AT); Mathias Kals, Grinzens (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 258 days.

(21) Appl. No.: 15/537,482

(22) PCT Filed: Dec. 17, 2015

(86) PCT No.: PCT/US2015/066228
§ 371 (c)(1),
(2) Date: Jun. 19, 2017

(87) PCT Pub. No.: WO2016/100587
PCT Pub. Date: Jun. 23, 2016

(65) Prior Publication Data
US 2018/0001089 A1    Jan. 4, 2018

Related U.S. Application Data

(60) Provisional application No. 62/093,540, filed on Dec. 18, 2014.

(51) Int. Cl.
*A61N 1/05* (2006.01)
*A61N 1/36* (2006.01)
(Continued)

(52) U.S. Cl.
CPC ....... *A61N 1/36038* (2017.08); *A61N 1/0541* (2013.01); *A61N 1/36036* (2017.08);
(Continued)

(58) Field of Classification Search
CPC .............. A61N 1/0541; A61N 1/36036–36039
See application file for complete search history.

(56) References Cited

U.S. PATENT DOCUMENTS

| 7,496,406 B1 | 2/2009 | Segel et al. |
| 2004/0172101 A1* | 9/2004 | Van Hoesel ....... A61N 1/36036 607/57 |

(Continued)

FOREIGN PATENT DOCUMENTS

WO    WO 2014/065831 A1    5/2014

OTHER PUBLICATIONS

International Searching Authority, International Search Report—International Application No. PCT/US15/66228, dated Feb. 26, 2016 together with the Written Opinion of the International Searching Authority, 17 pages.

(Continued)

*Primary Examiner* — Eric D. Bertram
(74) *Attorney, Agent, or Firm* — Sunstein Kann Murphy & Timbers LLP (57) ABSTRACT

A bilateral hearing implant system has a left side and a right side. There is an interaural time delay (ITD) processing module on each side that adjusts ITD characteristics of the stimulation signals based on defined groups of stimulation channels that include: i. an apical channel group on each side corresponding to a lowest range of audio frequencies up to a common apical channel group upper frequency limit, wherein a common number of one or more stimulation channels is assigned to each apical channel group, and wherein corresponding apical channel group stimulation channels on each side have matching bands of audio frequencies, and ii. one or more basal channel groups on each side corresponding to higher range audio frequencies above the apical channel group upper frequency limit.

17 Claims, 7 Drawing Sheets

(51) Int. Cl.
*A61N 1/372* (2006.01)
*H04R 25/00* (2006.01)

(52) U.S. Cl.
CPC ....... *A61N 1/37217* (2013.01); *H04R 25/505* (2013.01); *A61N 1/3727* (2013.01); *H04R 2225/67* (2013.01)

(56) References Cited

U.S. PATENT DOCUMENTS

| | | | |
|---|---|---|---|
| 2006/0100672 A1 | 5/2006 | Litvak | |
| 2008/0319509 A1* | 12/2008 | Laback | A61N 1/36036 607/57 |
| 2009/0264961 A1* | 10/2009 | Schleich | A61N 1/36032 607/57 |
| 2010/0249880 A1* | 9/2010 | Aschbacher | A61N 1/36036 607/57 |
| 2012/0303093 A1* | 11/2012 | Wouters | A61N 1/0541 607/57 |
| 2014/0052217 A1* | 2/2014 | Smith | A61N 1/0541 607/57 |
| 2014/0219486 A1* | 8/2014 | Brown | H04R 25/43 381/320 |
| 2015/0265837 A1* | 9/2015 | Kulkarni | H04R 25/407 381/313 |

OTHER PUBLICATIONS

Majdak et al., "Effects of interaural time differences in fine structure and envelope on lateral discrimination in electric hearing," *The Journal of the Acoustical Society of America*, vol. 120, No. 4, Oct. 2006, pp. 2190-2201.

* cited by examiner

BILATERAL MATCHING OF FREQUENCIES AND DELAYS FOR HEARING IMPLANT STIMULATION

This application is a 371 national phase entry of Patent Cooperation Treaty Application PCT/US2015/066228, filed Dec. 15, 2015, which in turn claims priority from U.S. Provisional Patent Application 62/093,540, filed Dec. 18, 2014, both of which are incorporated herein by reference in their entireties.

FIELD OF THE INVENTION

The present invention relates to hearing implant systems, and more specifically to signal processing arrangements in bilateral hearing implant systems.

BACKGROUND ART

Figure 1:
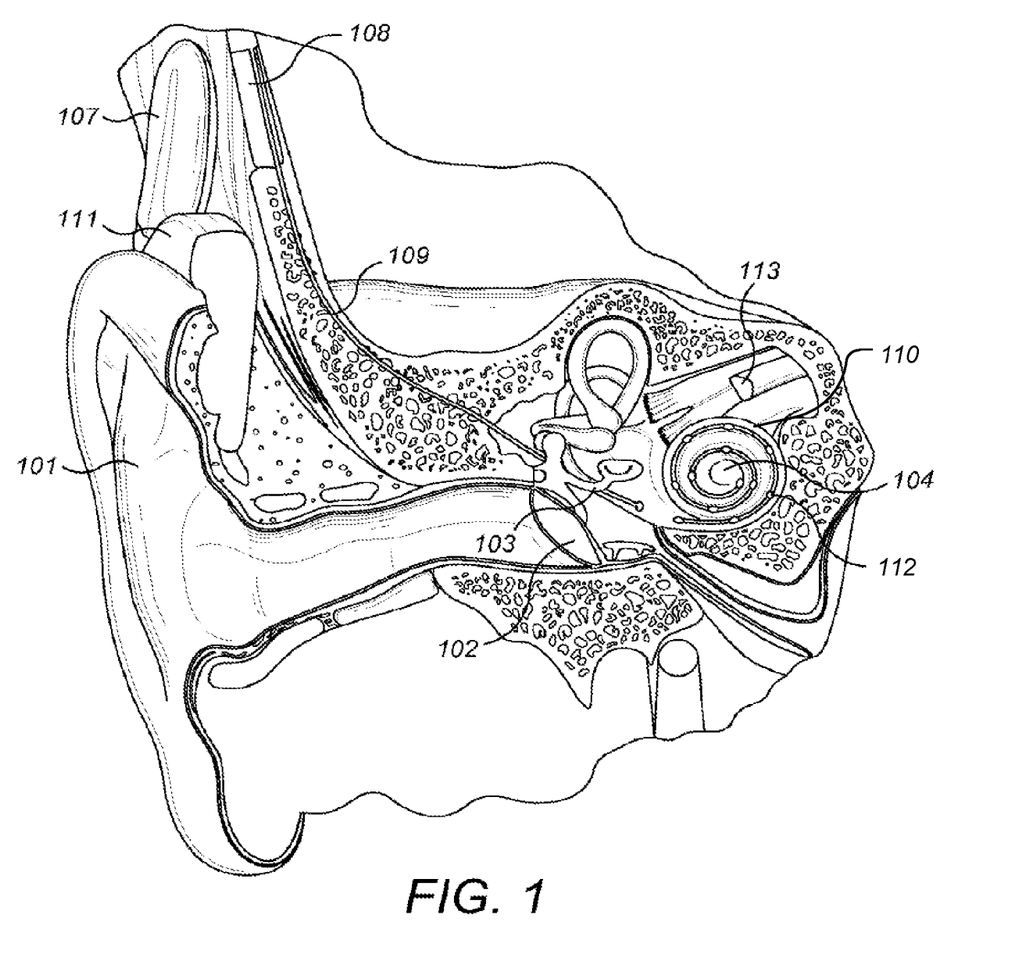
FIG. 1 shows a section view of a human ear with a typical auditory prosthesis system designed to deliver electric stimuli to the inner ear and acoustic stimuli at the ear canal.

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus hearing implant systems include brainstem implants, middle brain implants, etc. each stimulating a specific auditory target in the auditory system.

FIG. 1 also shows some components of a typical cochlear implant system where an external microphone provides an audio signal input to an external implant processor 111 in which various signal processing schemes can be implemented. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed audio signal is then converted into a digital data format for transmission by external transmitter coil 107 into an implant stimulator 108. Besides receiving the processed audio information, the implant stimulator 108 also performs additional signal processing such as error correction, pulse formation, etc., and produces stimulation signals (based on the extracted audio information) that are sent through an electrode lead 109 to an implanted electrode array 110. Typically, this electrode array 110 includes multiple electrode contacts 112 on its surface that provide selective stimulation of the cochlea 104.

Binaural stimulation has long been used in hearing aids, but it has only recently become common in hearing implants such as cochlear implants (CI). For cochlear implants, binaural stimulation requires a bilateral implant system with two implanted electrode arrays, one in each ear. The incoming left and right side acoustic signals are similar to those in hearing aids and may simply be the output signals of microphones located in the vicinity of the left and right ear, respectively.

Figure 2:
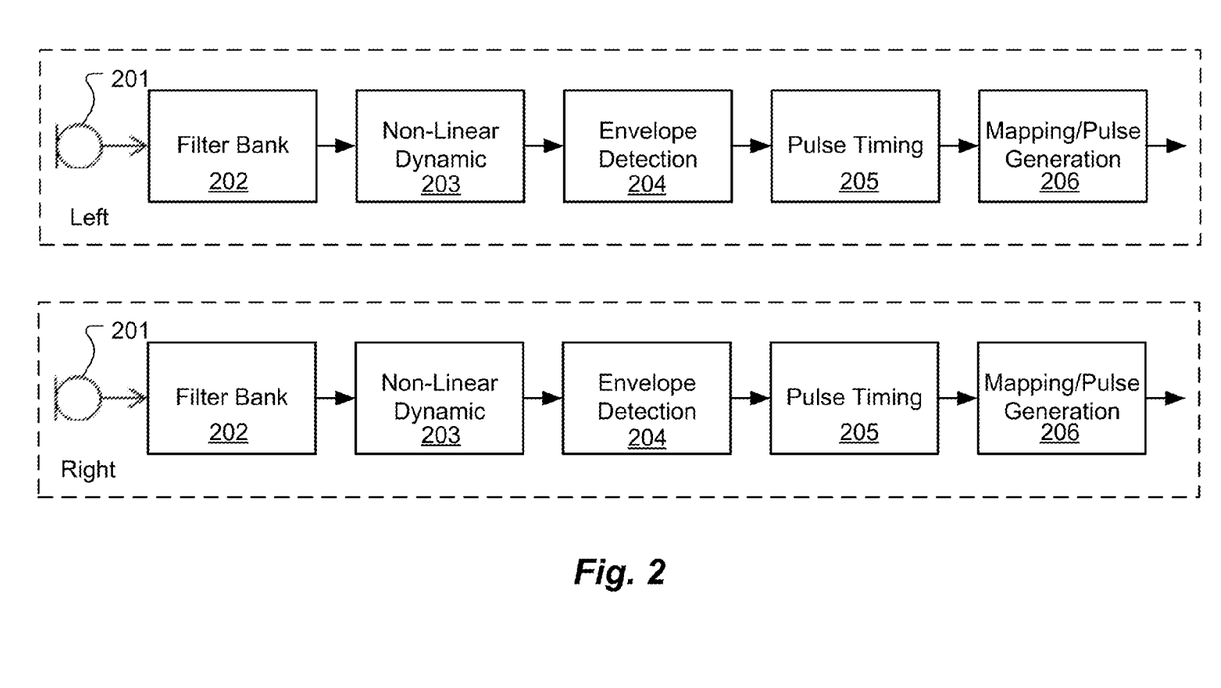
FIG. 2 shows various functional blocks in a typical bi-lateral cochlear implant signal processing arrangement.
Figure 3:
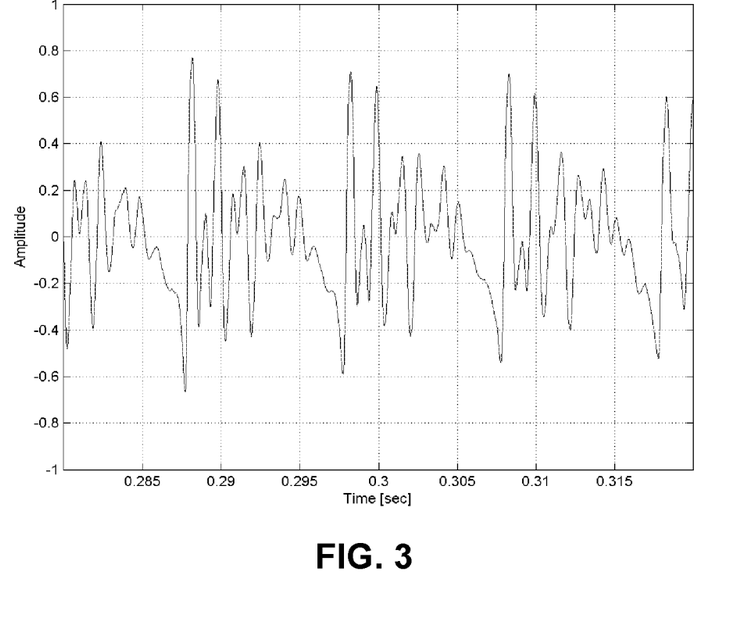
FIG. 3 shows an example of a short time period of an audio speech signal from a microphone.
Figure 4:
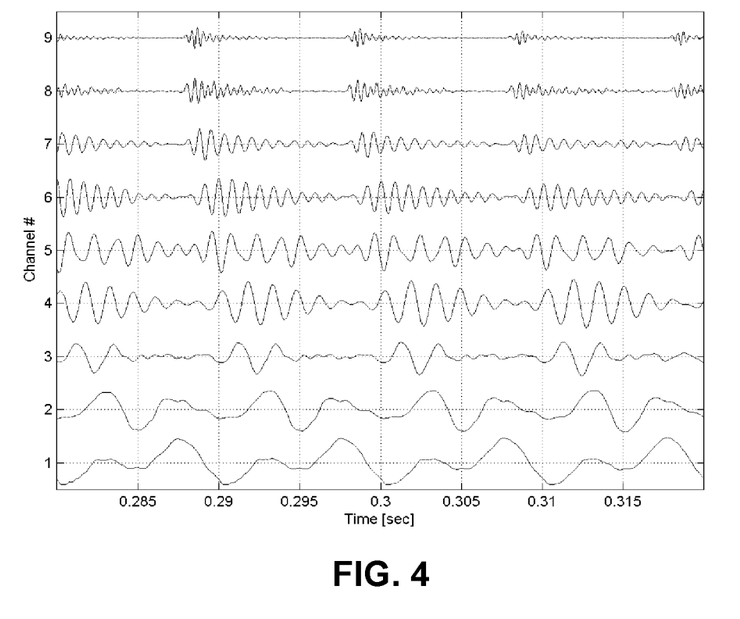
FIG. 4 shows an acoustic microphone signal decomposed by band-pass filtering by a bank of filters into a set of signals.
Figure 5:
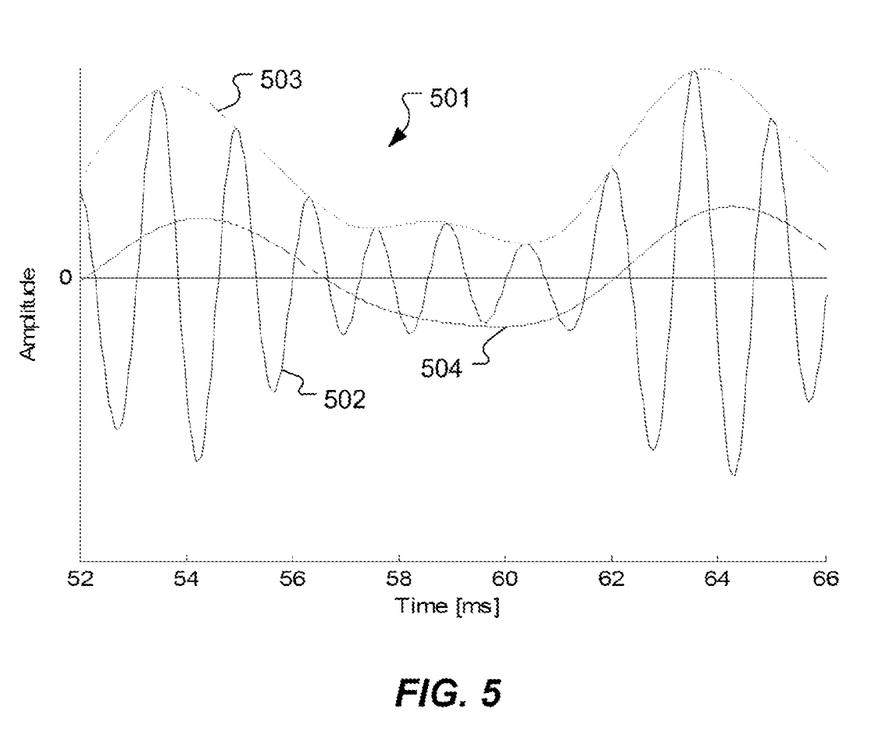
FIG. 5 shows a specific band pass signal and its various component parts.

FIG. 2 shows various functional blocks in a typical bilateral cochlear implant signal processing system. Independently on each side—left and right—an input sensing microphone 201 senses environmental sounds and coverts them into representative electrical signals that form audio inputs to the system. FIG. 3 shows a typical example of a short time period of an input audio signal from an input sensing microphone 201. The input audio signal is fed through multiple band pass filters (BPFs) 202 that decompose the input audio signal into multiple spectral band pass signals as shown, for example, in FIG. 4. As shown in FIG. 5, each band pass signal 501 is thought of as having a fine structure component 502 and an envelope component 503 (typically derived by Hilbert transformation). The filtered envelope signal 504 oscillates around the zero reference axis line with a frequency that is related to the fundamental frequency FO of the band pass filter.

A non-linear dynamic processing module 203 dynamically adjusts the filter envelopes by adaptive processing such as with automatic gain control (AGC) and other dynamic signal processing adjustments. Envelope detectors 204 extract the slowly-varying band pass envelope components of the band pass signals, for example, by full-wave rectification and low pass filtering. Pulse timing module 205 modulates the envelope signals with the corresponding band pass carrier waveforms to produce stimulation pulse requests on which the mapping/pulse generation module 206 performs a non-linear (e.g., logarithmic) mapping to fit the patient's perceptual characteristics and produces electrode stimulation signals in the specific form of non-overlapping biphasic output pulses for each of the stimulation contacts (EL-1 to EL-n) of each electrode array implanted in each cochlea on the left and right sides reflecting the tonotopic neural response of the cochlea.

Bilateral cochlear implants provide the benefits of two-sided hearing which can allow a listener to localize sources of sound in the horizontal plane. That requires information from both ears such as interaural level differences (ILDs) and interaural time differences (ITDs). This is discussed further, for example, in Macpherson, E. A, and Middlebrooks, J. C., *Listener Weighting Of Cues For Lateral Angle: The Duplex Theory Of Sound Localization Revisited*, J. Acoust. Soc. Am. 111, 2219-3622, 2002, which is incorporated herein by reference. An ITD is a relative time shift between signals arriving at the left and right ear which is caused by different times for the signal to reach each ear when the source of sound is not within the median plane. An ILD is a similar difference in sound levels of signals entering the ears. Two-sided hearing also is known to make speech easier to understand in noise, and again the perception of ITD plays a pivotal role therein. This is explained more fully, for example, in Bronkhorst, A. W., and Plomp, R., *The Effect Of Head-Induced Interaural Time And Level Differences On Speech Intelligibility In Noise*, J. Acoust. Soc. Am. 83, 1508-1516, 1988, which is incorporated herein by reference.

In the perception of ITDs, two sources of ITD information can be perceived: ITD information from the signal envelope and ITD information from the signal fine structure. It has been found that the fine structure ITD information plays a more important role than the envelope ITD information for sound localization and for understanding of speech in noise. This has been shown, for example, in Wightman and Kistler, Factors Affecting The Relative Salience Of Sound Localization Cues in Binaural and Spatial Hearing in Real and Virtual Environments, edited by Gilkey, R. H., and Anderson, T. R., (Lawrence Erlbaum Associates, Mahwah, N.J., 1997); Smith et al., *Chimaeric Sounds Reveal Dichotomies In Auditory Perception*, in Nature 416, 87-90, 2002; Nie et al., *Encoding Frequency Modulation To Improve Cochlear Implant Performance In Noise*, IEEE Trans. Biomed. Eng. 52, 64-73, 2005; and Zeng et al., *Speech Recognition With Amplitude And Frequency Modulations*, Proc. Natl. Acad. Sci. 102, 2293-2298, 2005, all of which are incorporated herein by reference, 2005, all of which are incorporated herein by reference.

In older cochlear implant arrangements, the fine structure information was not used. Instead, the incoming sound was separated into a number of frequency bands, for each band the slowly-varying envelope was extracted, and this envelope information was used to modulate the amplitude of a high-frequency pulsatile carrier signal. In such conventional cochlear implants, the frequency and phase of the pulsatile carrier signal was simply dictated by the speech processor and not directly related to the fine structure of the incoming signal. Accordingly, with such known cochlear implants, only the envelope ITD information was available, and consequently, ITD perception was very limited.

More recent cochlear implant systems have been implemented in which the stimulation signals are comprised of stimulation pulses with a timing that is based on temporal events within the fine structure of the left and right side acoustic signals. For instance, such temporal events can be the peaks or zero crossings within the fine structure of the signal. Stimulation schemes for coding fine structure information have been described for example by U.S. Patent Publication 20040478675; U.S. Pat. No. 6,594,525; U.S. Patent Publication 2004136556; which are incorporated herein by reference, and in van Hoesel and Tyler, *Speech Perception, Localization, And Lateralization With Bilateral Cochlear Implants*, J. Acoust. Soc. Am. 113, 1617-1630, 2003; and Litvak et al., *Auditory Nerve Fiber Responses To Electric Stimulation: Modulated And Unmodulated Pulse Trains*, J. Acoust. Soc. Am. 110(1), 368-79, 2001, also incorporated herein by reference. With these improved stimulation strategies, the ITD perception should be increased as compared to stimulation strategies comprising envelope ITD information only. However, in comparative studies no improvement in sound localization or in the understanding of speech in noise environments has been found; See van Hoesel supra.

Hearing impaired listeners are also known to have difficulties with localizing sources of sound and understanding of speech in noisy environments. See for example, Colburn, S. et al. *Binaural Directional Hearing-Impairments And Aids* in W. Yost & G. Gourevitch (Eds.), Directional Hearing pp. 261-278, New York: Springer-Verlag, 1987; Durlach N. I. et al., *Binaural Interaction Of Impaired Listeners. A Review Of Past Research* in Audiology, 20(3):181-211, 1981; Gabriel K. J. et al. *Frequency Dependence Of Binaural Performance In Listeners With Impaired Binaural Hearing*, J Acoust Soc Am., January: 91(1):336-47, 1992; Hawkins and Wightman, *Interaural Time Discrimination Ability of Listeners with Sensorineural Hearing Loss*, Audiology. 19, 495-507, 1980; Kinkel, M. et al., *Binaurales Hören bei Normalhörenden and Schwerhörigen I. Meβmethoden und Meβergebnisse*, Audiologische Akustik 6/91, 192-201, 1991; Koehnke, J. et al., *Effects Of Reference Interaural Time And Intensity Differences On Binaural Performance In Listeners With Normal And Impaired Hearing*, Ear and Hearing, 16, 331-353, 1995; and Smoski, W. J. and Trahiotis, C., *Discrimination Of Interaural Temporal Disparities By Normal-Hearing Listeners And Listeners With High-Frequency Sensorineural Hearing Loss*, J Acoust Soc Am. 79, 1541-7, 1986, all of which are incorporated herein by reference.

Existing bilateral cochlear implant systems typically are not matched with regards to the frequency distribution of the stimulation channels on both sides. And a bilaterally-unmatched frequency distribution of the band pass filters may lead to different interaural time delays—a given frequency component of the common audio input signal will be delayed differently by the two systems. In the specific case of FIR band pass filters, the difference in the group delay typically may be in the range of milliseconds and therefore will hamper the use of ITD information by an unmatched bilateral implant system. The delay difference between the filters is most pronounced in low frequency stimulation channels where hearing implant users have been shown to be most sensitive to ITDs. This effect will be even more pronounced, if the number of activated stimulation channels differs between the two sides.

In U.S. Patent Publication 20090264961 (incorporated herein by reference in its entirety), a system is described that uses virtual stimulation channels to change tonotopic location of the frequency channels in order to match group delays for interaural delay perception. U.S. Patent Publication 20060100672 (incorporated herein by reference in its entirety) also uses virtual channels to match information. U.S. Pat. No. 7,496,406 (incorporated herein by reference in its entirety) describes using channel groups for fitting, but these groups are not optimized for ITD perception, and the channels are not bilaterally matched, nor are the delays of the stimulation channels within the groups matched.

SUMMARY OF THE INVENTION

Embodiments of the present invention are directed to systems and methods for bilateral hearing implant systems having a left side and a right side. There are multiple audio processing stages on each side that are configured to process input audio signals to generate corresponding neural tissue stimulation signals using a plurality of stimulation channels each having an assigned band of audio frequencies. The audio processing stages on each side include an interaural time delay (ITD) processing module configured for adjusting ITD characteristics of the stimulation signals based on defined groups of stimulation channels including: i. an apical channel group on each side corresponding to a lowest range of audio frequencies up to a common apical channel group upper frequency limit, wherein a common number of one or more stimulation channels is assigned to each apical channel group, and wherein corresponding apical channel group stimulation channels on each side have matching bands of audio frequencies; and ii. one or more basal channel groups on each side corresponding to higher range audio frequencies above the apical channel group upper frequency limit, wherein a common number of basal channel groups are defined on each side, and wherein one or more stimulation channels are assigned to each basal channel group. The ITD processing modules adjust the ITD characteristics of the stimulation channels so that each stimulation channel within a given channel group has matching ITD characteristics, and corresponding channel groups on each side have matching ITD characteristics.

In specific embodiments, multiple stimulation channels may be assigned to each apical channel group. At least one of the basal channel groups may have different numbers of stimulation channels on each side. In some embodiments, corresponding basal channel groups on each side may have different corresponding bands of audio frequencies, and/or corresponding stimulation channels within a given basal channel group may have different corresponding bands of audio frequencies. The assigned stimulation channels in at least one apical channel group may include an acoustic stimulation channel in a hybrid electric acoustic system (EAS) hearing implant. And the apical channel group upper frequency limit may correspond to a system-specific upper limit of fine structure coding. And in specific embodiments, there may be an ITD fitting module configured for defining the groups of stimulation channels and communicating the groups of stimulation channels to the left and right sides.

DETAILED DESCRIPTION OF SPECIFIC EMBODIMENTS

Embodiments of the present invention are directed to bilateral hearing implant systems that have defined groups of stimulation channels on each side arranged so that each stimulation channel within a given channel group has matching ITD characteristics, and corresponding channel groups on each side have matching ITD characteristics. The same overall signal delay can be achieved for each channel with corresponding center frequencies for both sides of a bilateral hearing implant system. The resulting matched system then can provide accurate ITD information for implanted users that enables them to localise sound sources and enjoy better speech understanding in challenging listening situations.

As a practical matter, there may be different numbers of active stimulation channels on each side. This can occur due to deactivation of channels during the fitting process due to adverse side effects of stimulation such as facial nerve stimulation, because of extracochlear position, shortcuts, etc. Different numbers of channels can also occur with different types of implants on each side. The more apical low frequency stimulation channels are more important to cochlear implant users for ITD perception and so these channels should be given priority.

Figure 6:
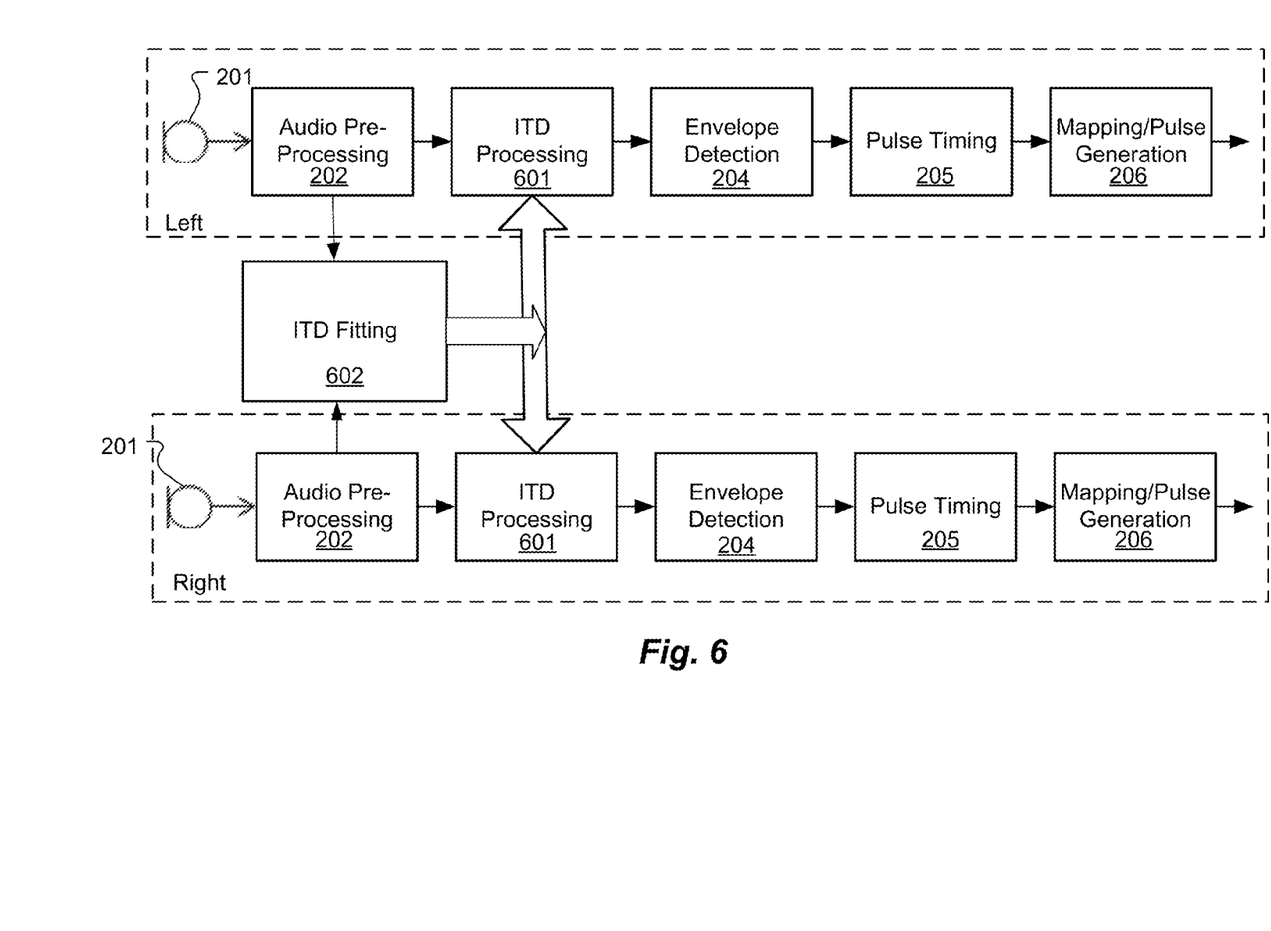
FIG. 6 shows various functional blocks in a bi-lateral cochlear implant signal processing arrangement with ITD adjusted channel groups according to one specific embodiment of the present invention.
Figure 7:
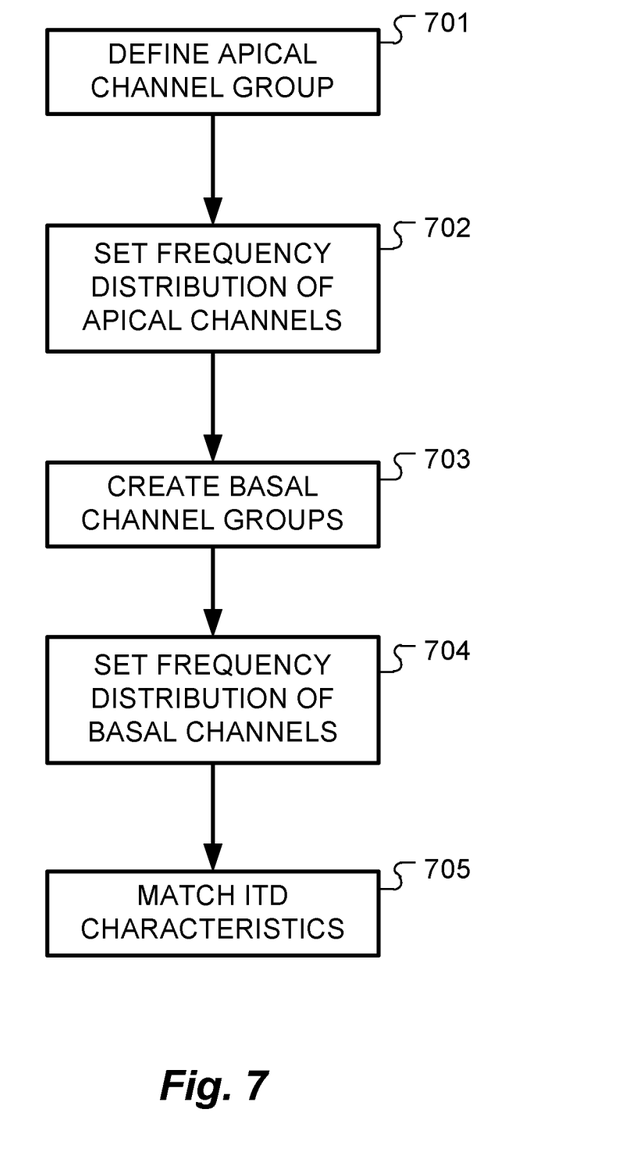
FIG. 7 shows various functional steps in organizing stimulation channels into ITD adjusted channel groups according to an embodiment of the present invention.

FIG. 6 shows various functional blocks in a bi-lateral hearing implant signal processing arrangement with stimulation channel grouping and FIG. 7 shows various functional steps in organizing stimulation channels into ITD adjusted channel groups according to one specific embodiment of the present invention. Just as in existing bilateral processing arrangements, left- and right-side audio inputs are generated by sensing microphones 201 and then processed by left-side and right-side audio pre-processing modules 202 that include filter banks configured to generate corresponding left-side and right-side band pass signals, where each band pass signal represents an associated band of audio frequencies in the audio input signals.

An ITD processing module 601 on each side adjusts the ITD characteristics of the stimulation signals based on defined groups of stimulation channels. In the specific embodiment shown in FIG. 6, the groups of stimulation channels are defined by an external ITD fitting module 602. Other embodiments may not require such an external fitting module 602 and the stimulation channel groups may be defined either by an internal module of the left and right sides, or there may be some other external means for defining the stimulation channel groups such as a pre-surgical software programming arrangement.

Defining of the stimulation channel groups includes defining an apical channel group for each side that corresponds to a lowest range of audio frequencies, step 701, up to some common apical channel group upper frequency limit. This involves assigning some common number of one or more apically located stimulation channels to the apical channel group on each side. The audio frequency bands of the stimulation channels in both apical channels groups are set to matching values, step 702. In a hearing implant system that transmits fine structure information, the apical channel group should be defined to cover the low frequency range that contains significant fine structure ITD perception for the patient user; for example, ITD detection thresholds less than 300 μsec. The frequency range for the apical channel group can also be defined by a system-specific upper limit of fine structure coding.

According to the number of activated electrodes N_activated of the side with the fewer number of activated stimulation channels, the number of channels in the apical group N_apical and its frequency distribution is set similarly on both sides. N_apical can be set to cover special frequency regions of the system, e.g. the region of fine structure stimulation. The selection of N_apical and the frequency distribution of the channels in the apical group can be derived by computation or by the usage of a lookup-table as, for example, in Table 1 or Table 2:

TABLE 1

Example for a logarithmic-based frequency
distribution in the apical channel group.

| | N_activated | | | | | |
|---|---|---|---|---|---|---|
| | 12 | 11 | 10 | 9 | 8 | 7 |
| | | | N_apical | | | |
| | 4 | 4 | 4 | 3 | 3 | 2 |
| Frequency Range for apical group [Hz] | 100-700 | 100-800 | 100-950 | 100-700 | 100-850 | 100-600 |
| Bandwidth channel 1 | 60 | 70 | 80 | 90 | 100 | 140 |
| Bandwidth channel 2 | 100 | 110 | 130 | 170 | 210 | 360 |
| Bandwidth channel 3 | 170 | 190 | 230 | 330 | 430 | N/A |
| Bandwidth channel 4 | 270 | 320 | 410 | N/A | N/A | N/A |

TABLE 2

Example for a linear frequency distribution
in the apical channel group.

| | N_activated | | | | | |
|---|---|---|---|---|---|---|
| | 12 | 11 | 10 | 9 | 8 | 7 |
| | | | N_apical | | | |
| | 4 | 4 | 4 | 3 | 3 | 2 |
| Frequency Range for apical group [Hz] | 100-700 | 100-800 | 100-950 | 100-700 | 100-850 | 100-600 |
| Bandwidth channel 1 | 150 | 175 | 212 | 200 | 250 | 250 |
| Bandwidth channel 2 | 150 | 175 | 212 | 200 | 250 | 250 |
| Bandwidth channel 3 | 150 | 175 | 212 | 200 | 250 | N/A |
| Bandwidth channel 4 | 150 | 175 | 212 | N/A | N/A | N/A |

This provides the same number and frequency distributions of the apical channel groups on both sides of the system.

The stimulation channels that are not in the apical groups are referred to as basal channels. The frequency distributions of the basal channels on both sides are set to cover the remaining frequency range. For higher range audio frequencies above the apical channel group upper frequency limit, one or more basal channel groups are defined on each side, step 703, specifically defining the same number basal channel groups on each side. One or more stimulation channels is assigned to each basal channel group that is defined, and the same number of basal groups is defined on each side, each covering the same frequency range. The audio frequency bands are also defined for each of the stimulation channels assigned to each basal channel group, step 704.

Possible frequency distributions for the channels in the apical or basal channel groups may be logarithmic distributions. For example the basal channel group frequency distributions can be equal logarithmic frequency intervals, for example, calculated in MATLAB code by:

logspace (log 10 (FlBasal), log 10 (FuBasal), nchan+1)

where FlBasal is the lower frequency boundary of the basal channels, FuBasal is the upper frequency boundary of the basal channels, and nchan is the number of basal channels.

Figure 8:
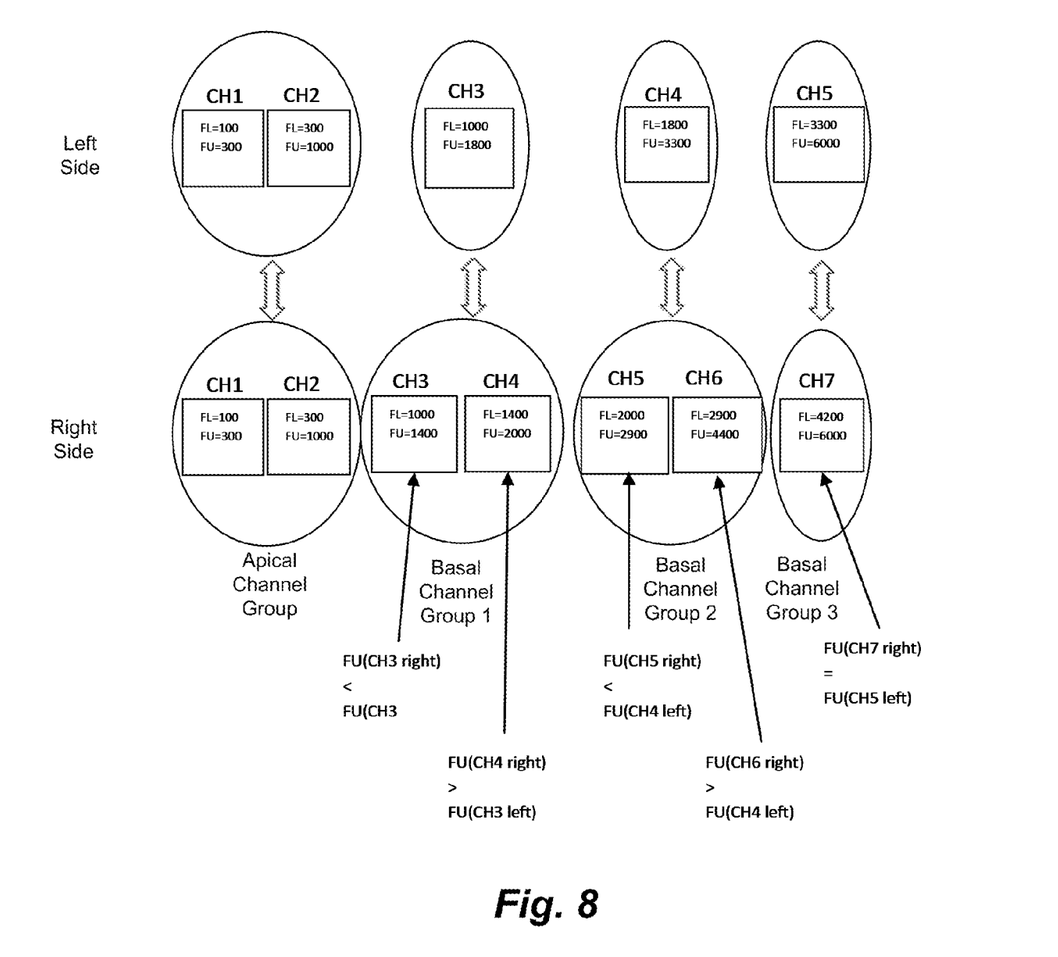
FIG. 8 shows an example of channel groups in a bilateral hearing implant system according to an embodiment of the present invention.

FIG. 8 shows one example of stimulation channel groups in a bilateral hearing implant system according to an embodiment of the present invention. In this example, the apical channel group on each side has two stimulation channels each, where Channel 1 corresponds to the range of 100-300 Hz, and Channel 2 corresponds to the range of 300-1000 Hz. In this example, there are also three basal channel groups defined on each side, with the left-side having one stimulation channel in each basal group, and right-side having two stimulation channels in basal groups 1 and 2 and on stimulation channel in basal group 3. This would lead to three basal groups on both sides of the implant system, where the three groups on the left side consist of one channel in each group, with the right side having two groups of two channels and one group of one channel.

Basal channel groups are formed in order to have the same number of groups on each side. As a starting point, each basal stimulation channel forms one group. Then if the number of basal channels differs between left and right sides, channels are assigned to their next basal neighbour group, starting with the most apical basal channel on the side with more basal channels. Channels are put in the first basal group until the first channel in the apical to basal order has a higher upper frequency boundary $F_U$ than the first basal group of the contralateral side (i.e., the side with fewer channels). Then the next basal group is formed and again, channels are added to the group onto the side with more channels until the first channel has a higher $F_U$ than the first basal group of the contralateral side. The procedure is repeated for the remaining channels. In the example shown in FIG. 8, channel 3 and 4 of the right side (the side with more active channels) is assigned to basal group 1, channel 5 and 6 are assigned to the basal group 2, and channel 7 is assigned to basal group 3. For the left side which is the side with fewer activated channels, each basal channel forms a basal group.

The defining of the stimulation channel groups can reflect an assessment of patient-specific frequency ranges for significant ITD perception, for example, according to the method described in Laback et al., *Effects of Interaural Time Differences in Fine Structure and Envelope on Lateral Discrimination in Electric Hearing*, J Acoust Soc Am, 120(4), 2006 October, p. 2190-2201, which is incorporated herein by reference in its entirety. For a system where the left and right side processors fit themselves, the audio processors comprise a calculation module for carrying out the algorithm and cooperate to each other to group and align their filter banks and adjust the ITD delays according the algorithm. The calculation module may be part of a signal processing controller and implemented in software. That cooperation includes exchanging necessary input information for the algorithm such as N_activated, N_apical, apical channel group upper frequency limit, basal channel groups frequency limits, etc. This exchange between the left and right side processors may be accomplished by a communication module located in each processor. The communication module may be configured for wireless or wired communication. In a further embodiment, the exchange may be assisted by an external ITD fitting module 602 or any other suitable external interconnect. For a system where the stimulation channel groups are externally defined (e.g., by an external ITD fitting module) the channel group information may be stored in internal memory in a table that is programmed during e.g. a pre-surgical or post-surgical fitting session.

The ITD processing module 601 adjusts the ITD characteristics of the assigned stimulation channels for each channel group, step 705, so that each stimulation channel within a channel group has matching ITD characteristics and so that corresponding channel groups on each side have matching ITD characteristics. In a specific embodiment, the ITD processing module 601 may adjust the ITD characteristics of the channels or groups so as to match the delay of the channel or group having the lower upper frequency range $F_U$ because lower frequencies have longer group delays, so higher frequency channels/groups can be set to same total delay by adding additional delay. If a basal group has multiple channels, then delays are added to the filters of the channels so that all channels in that basal group will have the group delay of the filter of the most apical channel in this group. In the example of FIG. 8, channel 4 will be delay-matched to channel 3 and channel 6 will be delay matched to channel 5. Contralateral matching delays are applied to the channel of a basal group with the least delay, so that each basal group has the same overall delay as the corresponding group on the contralateral side. Multiple further audio processing stages are configured to use the organized stimulation channels to generate the hearing stimulation signals for the stimulation channels; for example, envelope detection module 204, pulse timing module 205, and mapping/pulse generation module 206, etc.

In some specific embodiments, further matching of the group delays on both sides can be achieved by adding specific delays to each basal channel, so that channels with corresponding center frequencies (contralateral channels with nearest center frequencies) have the same overall delay on both sides. In the example of FIG. 8, basal group 1 on the left side will have the same delay as basal group 1 on the right side etc. so that the interaural delay is the same for each group for stimuli with no ITD (coming from the front of an implanted user).

The assigned stimulation channels in at least one apical channel group may include an acoustic stimulation channel in a hybrid electric acoustic system (EAS) hearing implant. To ensure correct ITD perception in such an arrangement, the filter bank delay and frequency boundaries of the acoustic stimulation channels should be matched. Propagation times of traveling waves along the basilar membrane also should be considered. In a basic approach, the average propagation time up to the neurons for a selected frequency band as known in the literature can be used. In a more advanced approach, an electric model with corresponding time properties might be used. Based on the calculated complete acoustic and electric propagation time, the required compensation can be calculated and applied in the signal processing chain.

Further delay compensation can be performed for other analog parts of the implant system with production-related variations regarding signal delays, for example, for microphones and pre-amplification stages. One method to account for delays without implementing additional delay lines is to adjust the filter group delays on corresponding channels on each side by varying the frequency boundaries of the stimulation channels. That would require a compromise between delay matching and frequency matching. For example, channel 1 on the left side could be assigned to a frequency range of 100 to 300 Hz, and channel 1 on the right side to the range from 110 to 300 Hz, when the resulting overall delay of channel 1 can be equalized on the left and right side with this setting.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for hearing implants other than cochlear implants such as an auditory brainstem implant.

What is claimed is:

1. A bilateral hearing implant system having a left side and a right side, the system comprising:
   a plurality of audio processing stages on each side configured to process input audio signals to generate corresponding neural tissue stimulation signals using a plurality of stimulation channels each having an assigned band of audio frequencies;
   wherein the audio processing stages on each side include an interaural time delay (ITD) processing module configured for adjusting signal propogation time delays of the stimulation signals based on defined groups of stimulation channels including:
   i. an apical channel group on each side corresponding to a lowest range of audio frequencies up to a common apical channel group upper frequency limit, wherein a common number of one or more stimulation channels is assigned to each apical channel group, and wherein corresponding apical channel group stimulation channels on each side have matching bands of audio frequencies; and
   ii. one or more basal channel groups on each side corresponding to higher range audio frequencies above the apical channel group upper frequency limit, wherein a common number of basal channel groups are defined on each side, and wherein one or more stimulation channels are assigned to each basal channel group;
   wherein the ITD processing modules adjust the time delays of the stimulation channels so that:

iii. each stimulation channel within a given channel group has matching time delays, and
iv. corresponding channel groups on each side have matching time delays.

2. The system according to claim 1, wherein a plurality of stimulation channels are assigned to each apical channel group.

3. The system according to claim 1, wherein at least one of the basal channel groups has different numbers of stimulation channels on each side.

4. The system according to claim 1, wherein corresponding basal channel groups on each side have different corresponding bands of audio frequencies.

5. The system according to claim 1, wherein corresponding stimulation channels within a given basal channel group have different corresponding bands of audio frequencies.

6. The system according to claim 1, wherein the assigned stimulation channels in at least one apical channel group comprise an acoustic stimulation channel in a hybrid electric acoustic system (EAS) hearing implant.

7. The method according to claim 6, wherein the time delays are a function of both acoustic and electric propagation times.

8. The system according to claim 1, wherein the apical channel group upper frequency limit corresponds to a system-specific upper limit of fine structure coding.

9. The system according to claim 1, further comprising:
an ITD fitting module configured for defining the groups of stimulation channels and communicating the groups of stimulation channels to the left and right sides.

10. A method of providing stimulation in a bilateral hearing implant system having a left side and a right side, each side using a plurality of stimulation channels each having an assigned band of audio frequencies, the method comprising:
defining an apical channel group on each side corresponding to a lowest range of audio frequencies up to a common apical channel group upper frequency limit, wherein a common number of one or more stimulation channels is assigned to each apical channel group, and wherein corresponding apical channel group stimulation channels on each side have matching bands of audio frequencies;
defining one or more basal channel groups on each side corresponding to higher range audio frequencies above the apical channel group upper frequency limit, wherein a common number of basal channel groups are defined on each side, and wherein one or more stimulation channels is assigned to each basal channel group; and
adjusting propagation time delays of the stimulation channels so that:
i. each stimulation channel within a given channel group has matching time delays, and
ii. corresponding channel groups on each side have matching time delays;
processing input audio signals via the stimulation channels so as to generate corresponding neural tissue stimulation signals; and
providing the stimulation signals to neural tissue.

11. The method according to claim 10, wherein a plurality of stimulation channels are assigned to each apical channel group.

12. The method according to claim 10, wherein at least one of the basal channel groups has different numbers of stimulation channels on each side.

13. The method according to claim 10, wherein corresponding basal channel groups on each side have different corresponding bands of audio frequencies.

14. The method according to claim 10, wherein corresponding stimulation channels within a given basal channel group have different corresponding bands of audio frequencies.

15. The method according to claim 10, wherein the assigned stimulation channels in at least one apical channel group comprise an acoustic stimulation channel in a hybrid electric acoustic system (EAS) hearing implant.

16. The method according to claim 15, wherein the time delays are a function of both acoustic and electric propagation time.

17. The method according to claim 10, wherein the apical channel group upper frequency limit corresponds to a system-specific upper limit of fine structure coding.

* * * * *

UNITED STATES PATENT AND TRADEMARK OFFICE
CERTIFICATE OF CORRECTION

PATENT NO. : 10,493,273 B2  
APPLICATION NO. : 15/537482  
DATED : December 3, 2019  
INVENTOR(S) : Meister et al.

Page 1 of 1

It is certified that error appears in the above-identified patent and that said Letters Patent is hereby corrected as shown below:

In the Claims

In Column 12, Line 7:
Delete "and"

Signed and Sealed this
Eighteenth Day of February, 2020

Andrei Iancu
*Director of the United States Patent and Trademark Office*